United States Patent [19]
Christensen

[11] Patent Number: 5,944,760
[45] Date of Patent: Aug. 31, 1999

[54] PROSTHETIC FOOT WITH REINFORCING MEMBER

[75] Inventor: Roland Christensen, Fayette, Utah

[73] Assignee: Roland J. Christensen Family Limited Partnership, Fayette, Utah

[21] Appl. No.: 08/906,287

[22] Filed: Aug. 4, 1997

[51] Int. Cl.[6] ........................................... A61F 2/66
[52] U.S. Cl. ............................................. 623/55; 623/52
[58] Field of Search ........................................ 623/47–55

[56] References Cited

U.S. PATENT DOCUMENTS

| | | |
|---|---|---|
| 2,036,830 | 8/1936 | Rowley . |
| 2,453,969 | 11/1948 | Carter ........................................ 623/52 |
| 2,470,480 | 4/1949 | Fogg . |
| 2,640,200 | 7/1953 | Wisbrun . |
| 3,551,914 | 1/1971 | Woodall . |
| 4,547,913 | 10/1985 | Phillips . |
| 4,721,510 | 1/1988 | Cooper et al. ............................ 623/55 |
| 5,019,109 | 5/1991 | Voisin . |
| 5,037,444 | 8/1991 | Phillips . |
| 5,112,356 | 5/1992 | Harris et al. . |
| 5,116,384 | 5/1992 | Wilson et al. . |
| 5,181,932 | 1/1993 | Phillips ..................................... 623/52 |
| 5,290,319 | 3/1994 | Phillips . |
| 5,387,246 | 2/1995 | Phillips . |
| 5,507,838 | 4/1996 | Chen ......................................... 623/55 |
| 5,514,185 | 5/1996 | Phillips ..................................... 623/52 |
| 5,653,767 | 8/1997 | Allen et al. ............................... 623/52 |

FOREIGN PATENT DOCUMENTS

| | | | |
|---|---|---|---|
| 295807 | 12/1916 | Germany .................................. 623/55 |
| 560606 | 6/1977 | U.S.S.R. ................................... 623/55 |

Primary Examiner—David H. Willse
Attorney, Agent, or Firm—Thorpe, North & Western, L.L.P.

[57] ABSTRACT

A prosthetic foot, having a forefoot member and a heel member, is comprised of two separate members forming opposite halves of the foot generally about the longitudinal axis of the foot for simulating natural rotation of the toes of a real foot. The forefoot member of the foot forms a resilient arc extending from a fixture member to a toe position and has an attachment portion, a curvilinear spring portion, an arch portion, and a toe portion. The heel member extends between the forefoot member and a heel position and has an attachment portion and a heel portion. The heel member is preferably attached to the forefoot member by wrapping the members with a resin impregnated fibre. The foot preferably has a mating member such as a rib-and-groove type connection between the forefoot and heel members for preventing the forefoot and heel portions from sliding and rotating with respect to each other and thus prevents shear stress from being placed on the fibers holding the members together. The foot has a fixture member for attachment to a socket for receiving a stump of an amputee and may include an angle adjustment mechanism for adjusting the angle of the foot members with respect to the ground. The foot may include a secondary heel member in addition to the heel member, or primary heel member for supporting the primary heel member.

31 Claims, 8 Drawing Sheets

PROSTHETIC FOOT WITH REINFORCING MEMBER

BACKGROUND OF THE INVENTION

1. Field of the Invention

The present invention relates to a resilient prosthetic foot that has a reinforcement member to provide reinforcement, and has multiple forefoot members to simulate toe rotation. More particularly, the present invention relates to a prosthetic foot having at least two resilient forefoot members, at least one resilient heel member, and at least one resilient reinforcement member that is engaged after the forefoot or heel members move from a normal range of movement to an extreme range.

2. Prior Art

Many individuals have lost a limb for various reasons including war, accident, or disease. In most instances these individuals are not only able to live relatively normal lives, but physically active lives as well. Often times, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element such as a spring. As the user steps onto the foot, the user's weight compresses the spring. As the user moves forward, the user's weight comes off the foot and the energy stored in the spring is used to propel the user forward.

Examples of such energy storing, spring-like feet having a forefoot member and a heel member include U.S. Pat. Nos. 5,037,444 and 4,547,913. U.S. Pat. No. 5,037,444 issued Aug. 6, 1991 to Phillips discloses a prosthetic foot having a forefoot portion and a heel portion. The forefoot portion has an attachment section, a curvilinear spring section, an arch section, and a toe section formed integrally with one another. The heel portion is removably attached to the forefoot portion at the intersection of the arch and toe sections by a bolt and nut. An elastomeric wedge is inserted between the forefoot portion and the heel portion. U.S. Pat. No. 4,547,913 issued Oct. 22, 1985 to Phillips discloses a prosthetic foot having a forefoot portion and a heel portion. The forefoot portion and the heel portion are bound together with a "resin impregnated filament binding" by winding the filament around the members.

The stiffness of prosthetic feet typically vary according to the intended use. Feet intended for everyday use typically require a soft feel and thus incorporate a loose spring. Feet intended for athletic use typically require strength and thus incorporate a stiff spring. Although different feet may be changed to suit the particular activity, such switching is inconvenient and at times it is impossible, such as a sudden need to run to catch, or avoid being hit by, a bus. Feet designed for particular purposes are typically unsuited for other purposes. Stiff, athletic feet are too hard for everyday use, and loose, everyday feet are too fragile for athletic use. Multiple-use feet have been designed which are capable of many different uses, but without being particularly well suited for any use.

In addition, the performance of these energy storing feet has been altered in various ways, such as by using multiple springs in various configurations, using bladders or resilient materials disposed between various elements, and using multiple springs that deflect at different intervals of foot deflection to add resistance.

U.S. Pat. No. 5,290,319 issued Mar. 1, 1994 to Phillips discloses a prosthetic foot having a forefoot portion, a heel portion, and an auxiliary member disposed above the forefoot portion. A bladder is disposed between the auxiliary member and the forefoot portion. The pressure in the bladder is varied to adjust the performance of the foot. In this configuration, the auxiliary member is a structural member against which the bladder is compressed.

U.S. Pat. No. 5,387,246 issued Feb. 7, 1995 to Phillips discloses a prosthetic foot having a forefoot portion, a sole member, and an auxiliary or secondary stiffness member disposed above the forefoot portion. The secondary member adds stiffness to the foot when the foot is deflected sufficiently forward such as to engage the secondary member.

U.S. Pat. No. 4,721,510 issued Jan. 26, 1988 to Cooper et al. discloses a prosthetic foot having a relatively flexible primary foot member and a relatively stiff secondary foot member disposed above the primary foot member such that the spring force of the foot is increased as the primary foot member deflects to the secondary foot member.

One problem with all these configurations is that the foot forms a unitary member incapable of providing independent and multiple responses to uneven terrain, such as a slope. The unitary member is a platform that must rotate as a single body to conform to the slope of the terrain in an unnatural manner. Such a foot is incapable of rotating about a longitudinal axis.

Almost all of the past designs have focused on the major aspect of the prosthetic foot—movement of the ankle or foot as it relates to walking or running. Few designs consider the workings of the toes or the less conspicuous movements of the foot and ankle, such as the rotation of the foot and toes when the user stands on an incline. In a natural foot, the foot and toes rotate to conform to the slope of the terrain. The artificial foot of previous designs usually incorporates a unitary foot and toe platform that is incapable of such independent rotational movement or response.

U.S. Pat. No. 2,640,200 issued Jun. 2, 1953 to Wisbrun discloses a prosthetic foot having a steel, horizontal foot plate connected to a vertical leg post by two joints. The first joint has a head mounted in a diagonally mounted cylindrical bearing such that as the foot plate rotates downward it is also rotated inward and vice versa. The second joint permits limited vertical rotation by a T-head inserted through a slot, turned, and secured by a screw. An arm, attached to the leg post, extends over the foot plate and engages an inclined leaf spring. The purpose of the above construction is a more natural gait. The resulting motion of the above construction is the rotation of the foot plate down and inward as the user steps on the heel and then rotation upward and outward as weight is taken off the foot plate. Wisbrun also discloses that a slit may be provided in the forward end of the foot plate for "a more effective resilient up-thrust" as weight is taken off the foot plate. One problem with this configuration is the complexity of the several joints. There are numerous moving parts and joints subject to friction, wear, and failure. In addition, the slit in the foot plate does not simulate toe rotation.

U.S. Pat. No. 2,036,830 issued Apr. 7, 1936 to Rowley discloses a prosthetic foot having a shin member connected to a foot member by a bearing hinge. The foot member has a solid, inner core portion and a flexible exterior. The foot member also has a rigid member with a "pair of spaced apart prongs" extending between the core and the exterior and a pivot at the ball of the foot in contact with the prongs. The rigid member is operatively attached to a rubber block that expands and contracts between the shin member and core member as the user walks. Thus, the rigid member acts as a lever extending from the toe position to the ankle position and pivoting at the ball of the feet. As the user pivots forward on the foot, the rubber block is compressed and the ankle end of the rigid member is forced down and the toe end of the rigid member is forced up. As the user lifts the foot, the rubber block expands and the ankle end of the rigid member is forced up and the toe end of the rigid member is forced down. The purpose of the rigid member is to return the flexible toe portion to its normal position after being bent upwards by walking. One problem with this configuration is that the rigid prongs do not deflect or bend to simulate toe rotation. Nor do the rigid prongs pivot independently.

Another problem with both the above devices is that neither stores a substantial amount of energy. In addition, neither has a reinforcement member to vary the stiffness of the foot.

Therefore, it would be advantageous to develop a prosthetic foot capable of simulating the natural toe rotation of a real foot. It would also be advantageous to develop a prosthetic foot having a reinforcement member. In addition, it would be advantageous to develop a prosthetic foot having various degrees of stiffness.

OBJECTS AND SUMMARY OF THE INVENTION

It is an object of the present invention to provide a prosthetic foot capable of simulating the natural rotation of a real foot.

It is another object of the present invention to provide a prosthetic foot capable of various different stiffness through a range of motion of the foot.

It is yet another object of the present invention to provide a prosthetic foot with a reinforcement member to reinforce the forefoot, heel, or both.

These and other objects and advantages of the present invention are realized in a prosthetic foot having at least two forefoot members, at least one heel member, and at least one reinforcement member. In the preferred embodiment, the foot has a first and a second forefoot members coupled at an attachment location, near a socket for receiving a stump of an amputee, and extending to a toe location. The heal member is coupled near an arch portion of the forefoot member and extends to a heel location. Because the foot has a first and second forefoot member, the foot is able to respond to uneven terrain more like a natural foot having rotating toes. The heel member may also consist of a first and a second heel members.

The heel and forefoot members are resilient and deflect, or move, through a range of motion as a force is applied, such as the user's weight. A normal range of motion occurs during normal activity, such as walking. An extreme range of motion occurs during extreme activity, such as running. The heel and forefoot members also have a resistance response, such as a spring force or stiffness, to the applied force.

At least one resilient reinforcement member is coupled to the forefoot member and extends to a free section operable within the range of motion of any of the heel or forefoot members. In the preferred embodiment, a forefoot reinforcement member is coupled near the attachment section and extends to a free section operable within the extreme range of motion of the forefoot members. A heel reinforcement member is coupled to the forefoot reinforcement member and extends to a free section operable within the extreme range of motion of the heel member.

As the foot is used under normal activity, the heel and forefoot members move through a normal range of motion. As the foot is used under extreme activity, the heel and forefoot members move into the extreme range of motion and the reinforcement members are engaged to reinforce the heel and forefoot members. Therefore, the foot has a soft feel during normal use, but is reinforced by the reinforcement member during extreme use.

The reinforcement members may be engaged by contact with a surface, such as the ground or shoe, or by contact with the heel and forefoot members. Protrusions, such as tabs, may be formed on the reinforcement members to extend over the heel and forefoot members. Alternatively, the protrusion may be formed on the heel and forefoot members and extend under the reinforcement members.

A strap may be coupled to the free section of the reinforcement member and any of the heel or forefoot members. The strap helps prevent the heel and forefoot members from snapping back to an unstressed position after an applied force is removed.

The reinforcement member may take various configurations. It may be a single forefoot reinforcement member disposed between the forefoot members and extending between the attachment location and the free section. It may be a single heel reinforcement member coupled to the forefoot members at an arch portion or the attachment location or coupled to the reinforcement member. It may be both a forefoot and a heel reinforcement member.

The reinforcement member may comprise a plurality of reinforcement members. They may be disposed over the first and second forefoot members, or the first and second heel members. They may be disposed in layers such that more reinforcement members are engaged at various levels of activity.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention.

Figure 1:
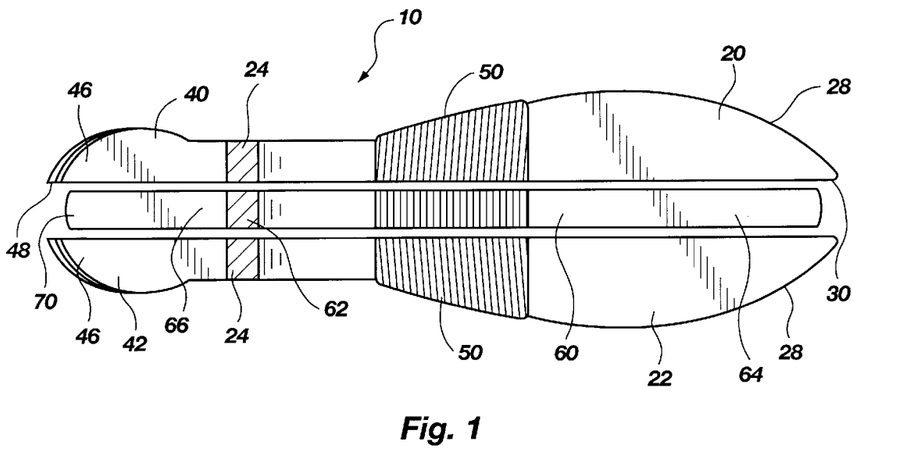
FIG. 1 is a top view of a prosthetic foot incorporating a preferred embodiment of the present invention.
Figure 2:
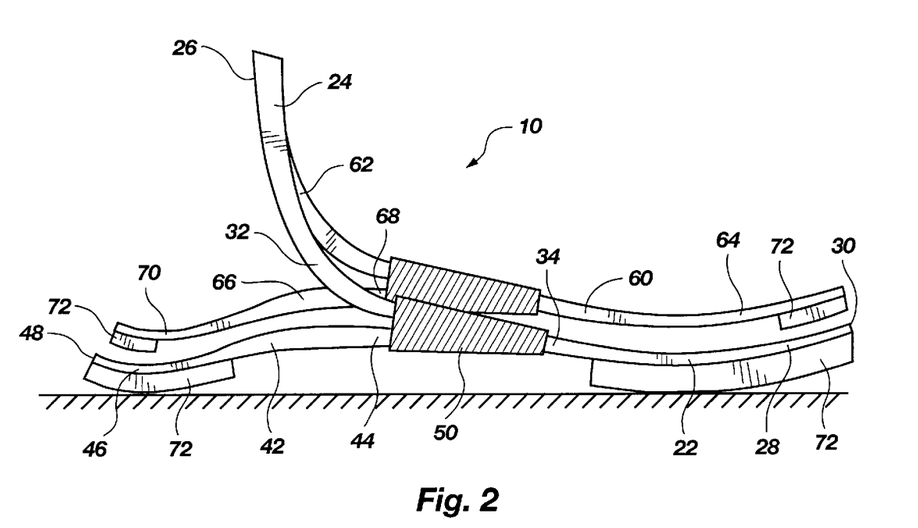
FIG. 2 is a side elevational view of the prosthetic foot incorporating a preferred embodiment of the present invention.

As illustrated in FIGS. 1 and 2, a preferred embodiment of a prosthetic foot 10 of the present invention is shown. The prosthetic foot 10 advantageously has at least two resilient forefoot members. In the preferred embodiment, the foot 10 has a first forefoot member 20 and a second forefoot member 22. The forefoot members 20 and 22 have base ends 24 coupled near an attachment location 26. The attachment location 26 is near a stump of an amputee and the base ends 24 of the forefoot members 20 and 22 attach to a socket (not shown) for receiving the stump of the amputee. The socket is configured for the specific needs of the amputee but typically has a portion adapted for standard attachment. The base ends 24 of the forefoot members 20 and 22 may be attached to the socket by any means such as by nut and bolt.

The forefoot members 20 and 22 extend forward from the base ends 24 to toe ends 28 at a general toe location 30. The toe location 30 is a region near the forward end of the foot where toes of a natural foot would be located.

The forefoot members 20 and 22 form a vertically oriented arc extending between the base ends 24 at the attachment location 26 and the toe ends 28 at the toe location 30. The forefoot members 20 and 22 have curvilinear spring portions 32 extending from the base ends 24 and arch portions 34 extending from the spring portions 32 to the toe ends 28.

The forefoot members 20 and 22 are preferably made of a resilient material. As the user steps, or pivots forward, on the prosthetic foot 10, the forefoot members 20 and 22 deflect. Because the forefoot members 20 and 22 are made of a resilient material, the forefoot members act as springs and store the energy to be released as the user moves forward.

The forefoot members 20 and 22 have a range of motion with multiple stages of advancement. The members engage a surface, such as the ground, either directly or through a shoe. As the user steps, or pivots forward, on the prosthetic foot 10, an applied force, such as the users weight, causes the members to deflect through the range of motion. The range of motion includes at least a normal range and an extreme range. The forefoot members 20 and 22 move through the normal range during normal activity, and through the normal range and into the extreme range during extreme activity. The normal activity includes activities such as walking and standing. The extreme activity includes activities which deflect the forefoot members beyond the normal range and deflection, such as when running and jumping.

The forefoot members 20 and 22 also have a resistance response to an applied force. The resistance response is the stiffness or spring force exerted by the members in response to the applied force. The applied force includes the static weight of the user and dynamic impact forces exerted on the foot during use.

The prosthetic foot 10 has at least one resilient heel member. In the preferred embodiment, the foot 10 has a first heel member 40 and a second heel member 42. The heel members 40 and 42 have base ends 44 coupled to the forefoot members 20 and 22. The base ends 44 preferably couple to the forefoot members 20 and 22 at the arch portions 34. The heel members 40 and 42 extend rearward from the base ends 44 to heel ends 46 at a general heel location 48. The heel location 48 is a region near the rearward end of the foot where the heel of a natural foot would be located. The heel members 40 and 42 preferably form an arc extending between the base ends 44 and the heel ends 46 at the heel location 48.

It is of course understood that the heel members may be coupled to the forefoot members at any appropriate location, including the attachment location. In addition, the heel members may comprise a single heel member.

The heel members 40 and 42 may be attached to the forefoot members 20 and 22 by wrapping the base ends 44 of the heel members and the arch portion 34 of the forefoot members with a resin impregnated fiber 50. Alternatively, any appropriate means may be used including bolting or even forming the heel members integrally with the forefoot members.

The heel members 40 and 42 are also made of a resilient material. As the user steps on the prosthetic foot 10, the heel members 40 and 42 deflect. Because the heel members 40 and 42 are made of a resilient material, they act as springs and cushion the force of the foot 10 as it contacts the ground and store energy.

The heel members 40 and 42 also have a range of motion with multiple stages of advancement. The members engage a surface, such as the ground, either directly or through a shoe. As the user steps on the prosthetic foot 10, an applied force, such as the users weight, causes the members to deflect through the range of motion. The range of motion includes at least a normal range and an extreme range. The heel members 40 and 42 move through the normal range during normal activity, and through the normal range and into the extreme range during extreme activity. The heel members 40 and 42 also have a resistance response to an applied force.

The first and second forefoot members 20 and 22, as well as the first and second heel members 40 and 42, are disposed adjacent one another with a space or gap separating them. The forefoot members 20 and 22, and the heel members 40 and 43, are independently movable with respect to each other. The forefoot members, and the heel members, may be mirror images of one another. Alternatively, the first and second forefoot members 20 and 22 may be configured to resemble an actual foot.

Because the foot 10 is advantageously composed of two forefoot members 20 and 22 and two heel members 40 and 42, the foot 10 is able to respond to uneven terrain more like a natural foot with rotating toes. In addition, the foot 10 is better able to simulate toe and axial foot rotation. Furthermore, first and second members of either the forefoot and/or heel may have different spring forces, or stiffness, to better simulate a natural foot. Therefore, the multiple member forefoot of the present invention presents a significant improvement over prior art feet by providing multiple members to respond as multiple toes of a real foot would respond and by providing forefoot members of varying stiffness to simulate the varying strengths of individual toes of a real foot.

The prosthetic foot 10 also advantageously has at least one resilient reinforcement member. The reinforcement member has a base section coupled to the forefoot members and extends to a free section. The free section operates within the extreme range of motion of any of the forefoot members or heel members and is freely moveable with respect to the members. The reinforcement member influences the range of motion and resistance response of any of the forefoot members or heel members.

In the preferred embodiment, the foot 10 has at least one forefoot reinforcement member 60. The forefoot reinforcement member 60 has a base section 62 coupled to at least one of the forefoot members 20 and 22. The base section 62 is preferably coupled with both forefoot members 20 and 22 near the attachment location 26. The forefoot reinforcement member 60 extends forward to a free section 64. The free section 64 of the reinforcement member 60 is not rigidly attached to the foot 10, but is freely moveable with respect to the foot. The free section 64 may be non-rigidly coupled to the forefoot or heel members as discussed below. The free section 64 operates within the extreme range of motion of the forefoot members.

In addition, the foot 10 preferably has at least one heel reinforcement member 66. The heel reinforcement member 66 has a base section 68 coupled to the forefoot reinforcement member 60. The heel reinforcement member 66 extends rearward to a free section 70. The free section 70 operates within the extreme range of motion of the heel members 40 and 42.

In normal use, the heel members 40 and 42 deflect, or move, through the normal range of motion as the user steps onto the foot 10. The heel members 40 and 42 engage the surface and the applied force of the user's weight causes the members to deflect. The forefoot members 20 and 22 also deflect, or move, through the normal range of motion as the user pivots forward on the foot 10. The forefoot members 20 and 22 engage the surface and the applied force of the user's weight causes the members to deflect. The normal range of motion is a result of normal activities, such as walking, that exert a normal applied force on the foot.

During extreme activities, such as running, a more extreme applied force is exerted on the foot resulting in an extreme range of motion. The greater the force exerted on the foot, the greater the deflection, or movement in the range of motion. In extreme use, the heel members 40 and 42 move through the normal range of motion and into the extreme range of motion. As the heel members move into the extreme range of motion, the free section 70 of the heel reinforcement member engages the surface and deflects with the heel members. Likewise, as the forefoot members move into the extreme range of motion, the free section 64 of the forefoot reinforcement member engages the surface and deflects with the forefoot members. During extreme activities, the reinforcement members are advantageously engaged to add stiffness and strength to the foot. Because of the reinforcement members, softer or less resistant heel and forefoot members may be used for a softer, more cushioned feel without the fear of failure or need to change prosthetics should the need for greater activity arise.

The present invention provides a significant improvement is over prior art prosthetic feet by providing a multipurpose foot, having a reinforcement member to add stiffness during extreme activities while maintaining the softer heel and forefoot members during normal activities, and by providing a foot that simulates toe rotation, having at least a first and second forefoot members capable of independent movement.

Cushions 72 may be disposed on the heel, forefoot, and reinforcement members to soften or cushion the contact between the members and the surface. These cushions may be attached to the forefoot for providing initial contact, or may be positioned for engagement upon deflection to some predetermined degree.

Figure 3:
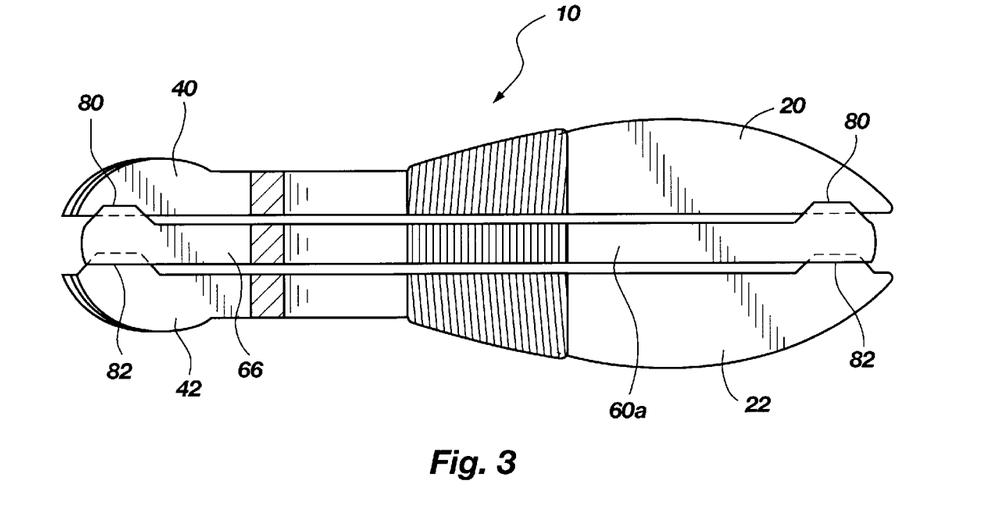
FIG. 3 is a top view of an alternative embodiment of the prosthetic foot of the present invention.

As illustrated in FIG. 3, the prosthetic foot 10 may also have protrusions formed on any of the reinforcement members or heel and forefoot members so that the reinforcement members are engaged by the heel and forefoot members as they move into the extreme range of motion, as opposed to being engaged by the surface. The protrusions may be formed on the reinforcement members, shown at 80, and extend out over the heel and forefoot members. Alternatively, the protrusions may be formed on the heel and forefoot members, shown at 82, and extend under the reinforcement members. The protrusions may be any suitable means of having the heel and forefoot members engage the reinforcement members, such as tabs, plates or rods.

Figure 4:
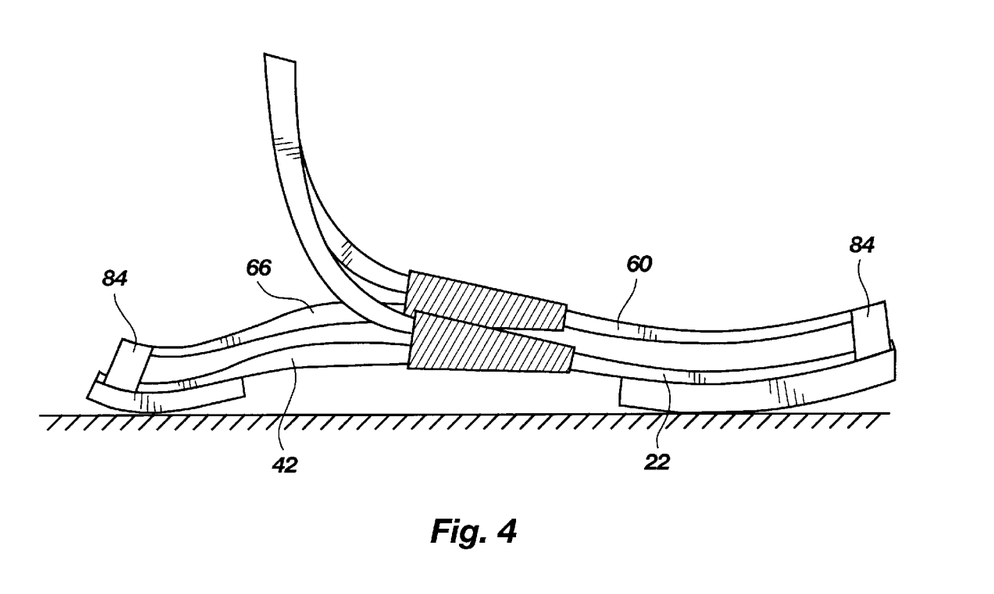
FIG. 4 is a side elevationel view of an alternative embodiment of the prosthetic foot of the present invention.

As illustrated in FIG. 4, the prosthetic foot 10 may also have a strap 84 coupled between the reinforcement members and any of the heel and forefoot members. The strap limits the heel or forefoot member from abruptly returning to an unstressed position when the applied force is removed. In other words, the strap helps prevent the heel and forefoot members from snapping back. The straps also transfer some of the heel load to the toe member under heel loading and some of the toe load to the heel members during toe loading. The strap may be any suitable means for coupling the reinforcement member to the heel or forefoot member, such as a nylon cord or wire cable. It may also comprise a resilient polymer.

Figure 5:
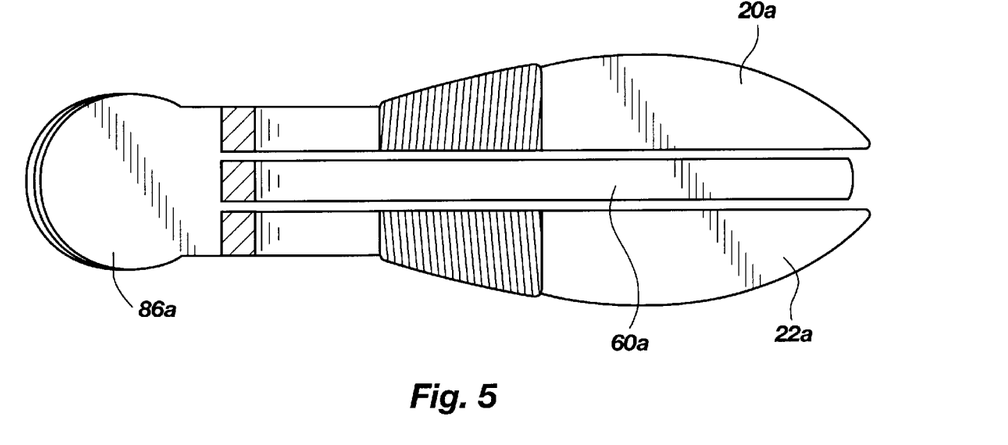
FIG. 5 is a top view of an alternative embodiment of the prosthetic foot of the present invention.
Figure 6:
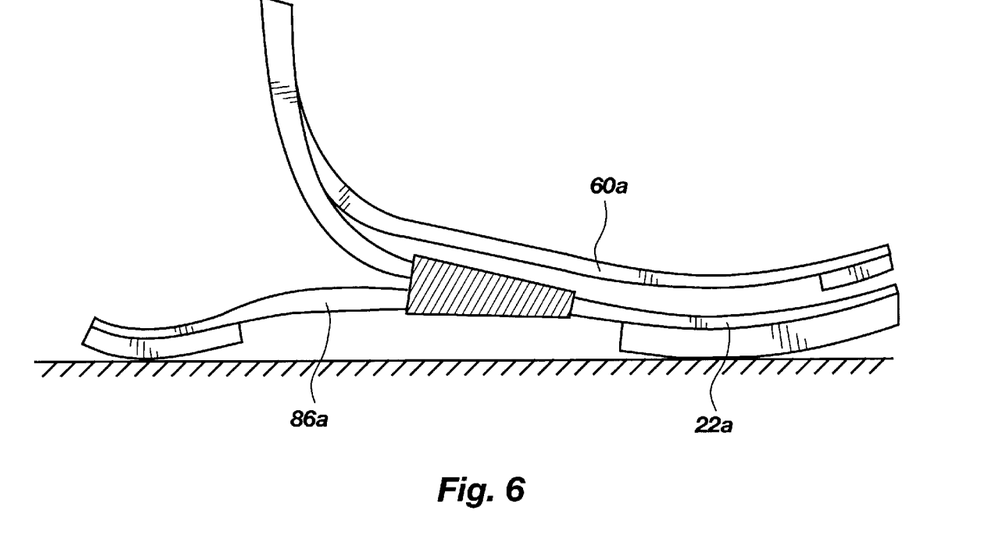
FIG. 6 is a side elevational view of an alternative embodiment of a prosthetic foot of the present invention.

The configuration of the reinforcement member with respect to the heel and forefoot members may take various forms, examples of which are illustrated and described in the alternative embodiments. As illustrated in FIGS. 5 and 6, the at least one reinforcement member may be a single, forefoot reinforcement member 60 disposed between the first and second forefoot members 20 and 22 similar to the preferred embodiment. As also illustrated in FIG. 5, the at least one heel member may be a single heel member 86.

Figure 7:
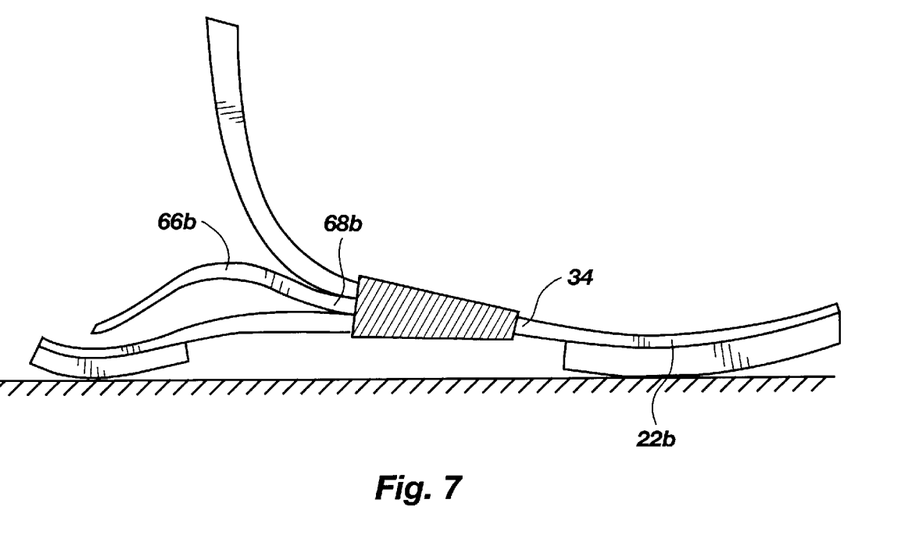
FIG. 7 is a side elevational view of an alternative embodiment of a prosthetic foot of the present invention.
Figure 8:
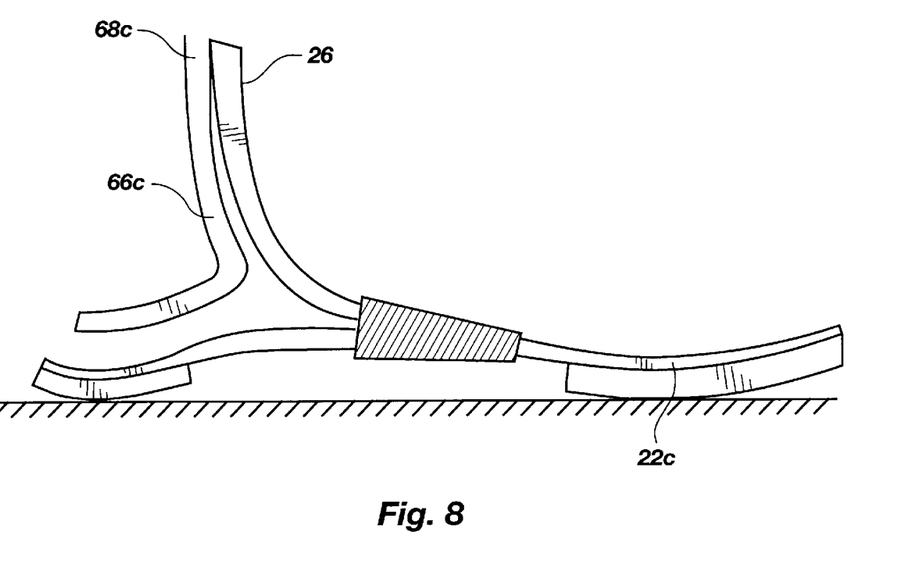
FIG. 8 is a side elevational view of an alternative embodiment of a prosthetic foot of the present invention.

As illustrated in FIGS. 7 and 8, the at least one reinforcement member may be a single, heel reinforcement member 66. The heel reinforcement member 66 may have the base section 68 coupled to the forefoot members 20 and 22 at the arch location 34 and between the forefoot members and the at least one heel member, as shown in FIG. 7. Alternatively, the heel reinforcement member 66 may have the base section 68 coupled 69 to the forefoot members 20 and 22 at the attachment location 26.

Figure 9:
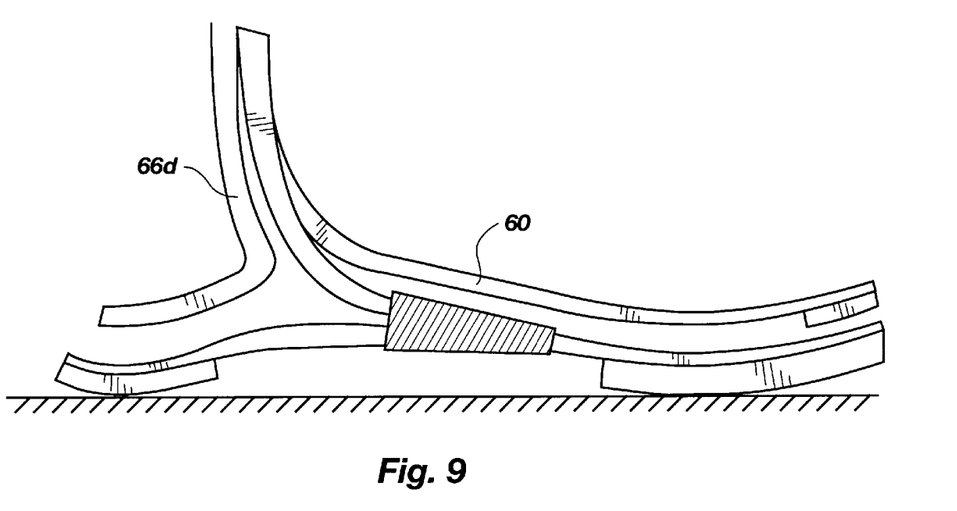
FIG. 9 is a side elevational view of an alternative embodiment of a prosthetic foot of the present invention.
Figure 10:
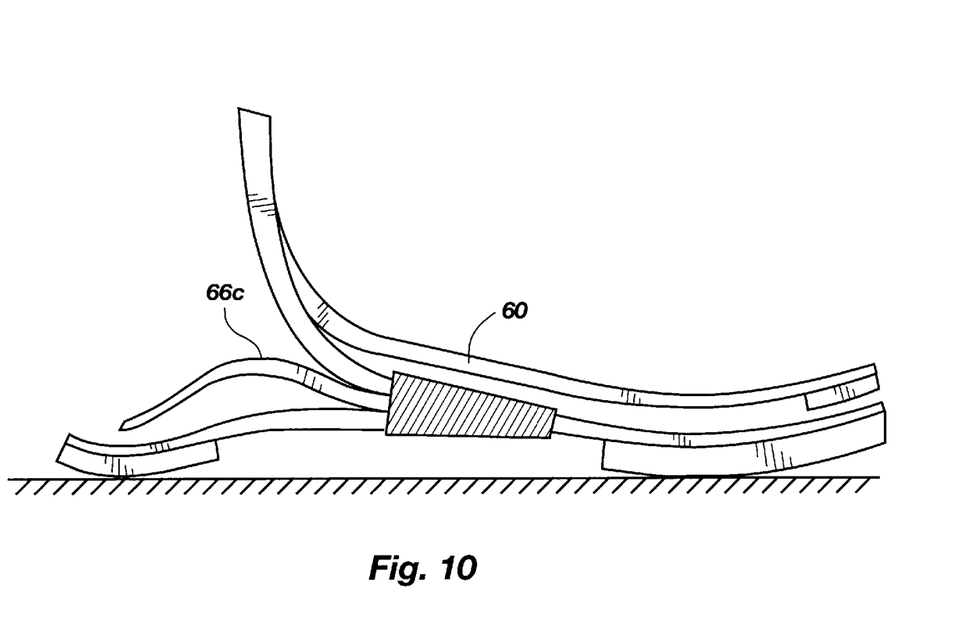
FIG. 10 is a side elevational view of an alternative embodiment of a prosthetic foot of the present invention.

As illustrated in FIGS. 9 and 10, the at least one reinforcement member may be a forefoot reinforcement member 60 and a heel reinforcement member 66.

Figure 11:
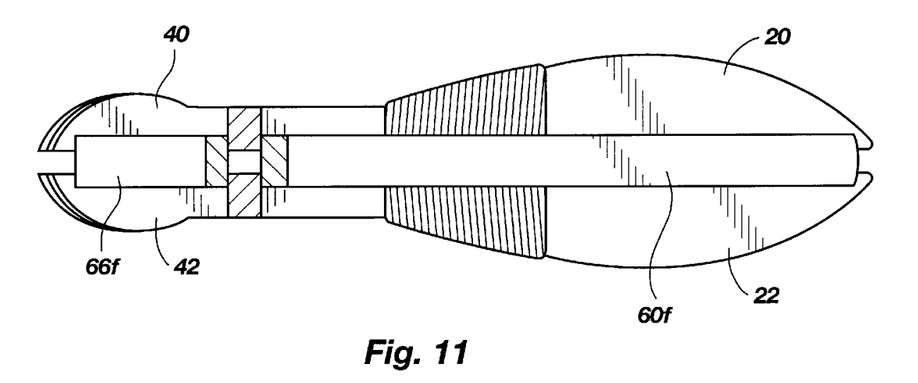
FIG. 11 is a top view of an alternative embodiment of the prosthetic foot of the present invention.

As illustrated in FIG. 11, the reinforcement members 60 and 66 may be disposed so that a portion of the reinforcement member is directly above the heel or forefoot member. In this way, the reinforcement member is engaged directly by the heel or forefoot member as they move into the extreme range of motion without the need for a protrusion.

Figure 12:
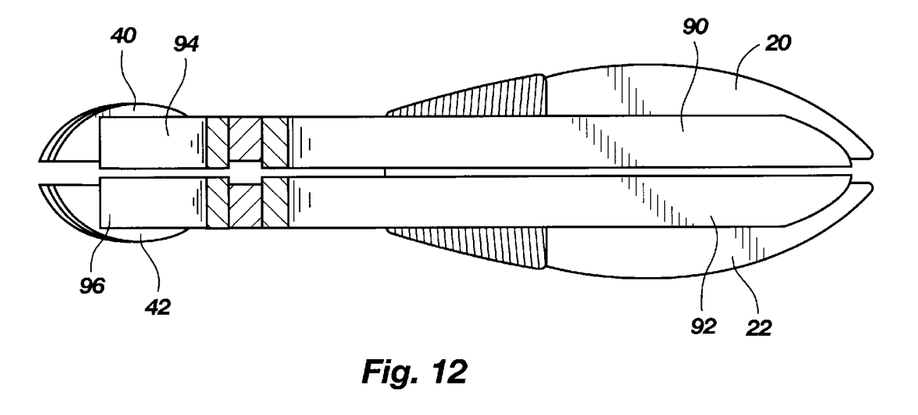
FIG. 12 is a top view of an alternative embodiment of the prosthetic foot of the present invention.

As illustrated in FIG. 12, the at least one reinforcement member may be a first forefoot reinforcement member 90, a second forefoot reinforcement member 92, a first heel reinforcement member 94, and/or a second heel reinforcement member 96. The first and second forefoot reinforcement members 90 and 92 may be disposed over the first and second forefoot member 20 and 22 respectively. Likewise, the first and second heel reinforcement members 94 and 96 may be disposed over the first and second heel members 40 and 42 respectively. In this way, the strengths or stiffness of the different reinforcement members, as well as the heel and forefoot members, may be varied to obtain the desired response and characteristic of the foot 10.

Figure 13:
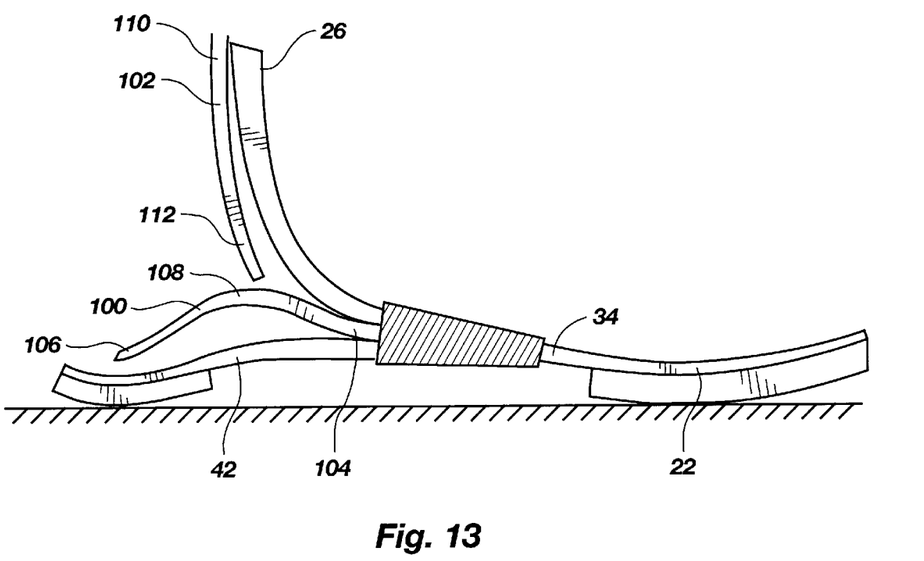
FIG. 13 is a side elevational view of an alternative embodiment of a prosthetic foot of the present invention.

As illustrated in FIG. 13, the at least one reinforcement member may be a first heel reinforcement member 100 and a second heel reinforcement member 102. The first heel reinforcement member 100 has a base section 104 coupled to the forefoot reinforcement members 20 and 22 near the arch section 34 and extends to a free section 106 operable within the extreme range of motion of the heel member. The first heel reinforcement member 100 forms an arcuate section 108. The second heel reinforcement member 102 has a base section 110 coupled to the first and second forefoot members 20 and 22 near the attachment section 26 and extends to a free section 112 near the arcuate section 108 of the first reinforcement member 100. In this way, the first heel reinforcement section 100 reinforces the heel member as the heel member enters into a first stage of extreme range of motion while the second heel reinforcement member 102 reinforces the first heel reinforcement member 100 at a second, more extreme range of motion. The second heel reinforcement member also helps reinforce the forefoot members as the free section 112 abuts the arcuate section 108 of the first heel reinforcement member 100.

Figure 14:
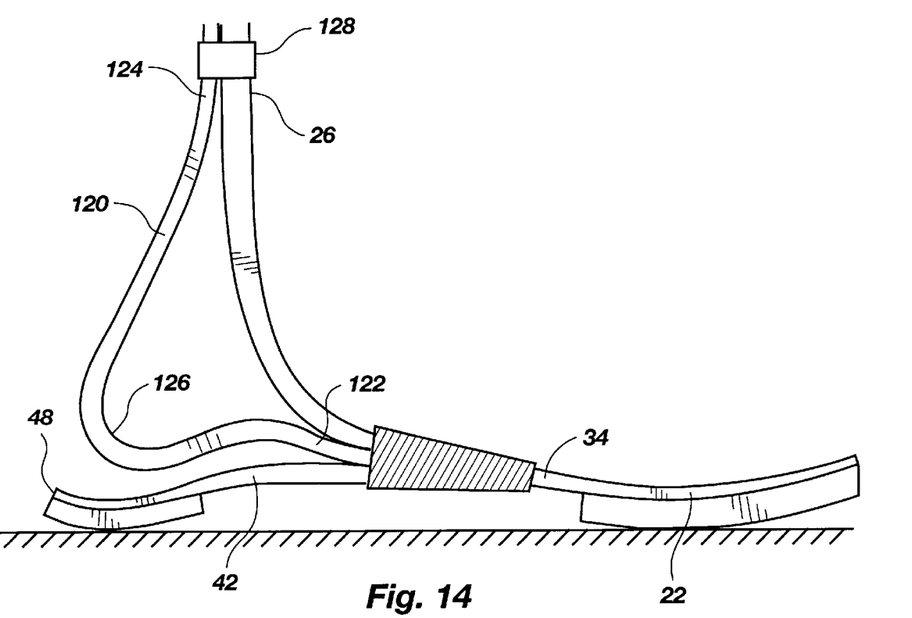
FIG. 14 is a side elevational view of an alternative embodiment of a prosthetic foot of the present invention.

As illustrated in FIG. 14, the prosthetic foot has a reinforcement member 120 with a base section 122 coupled to the first and second forefoot members 20 and 22 near the arch location 34. The reinforcement member 120 extends to a free section 124 near the attachment location 26. The reinforcement member 120 forms an arcuate section 126 that extends near the heel location 48. In this configuration, the reinforcement member 120 reinforces both the heel member and forefoot members. The arcuate section 126 is engaged as the heel member moves into the extreme range of motion. A strap 128 couples the free section of the reinforcement member 120 to the forefoot members 20 and 22. As the forefoot members 20 and 22 move into the extreme range of motion, the reinforcement member 120 acts as an additional forefoot member.

Figure 15:
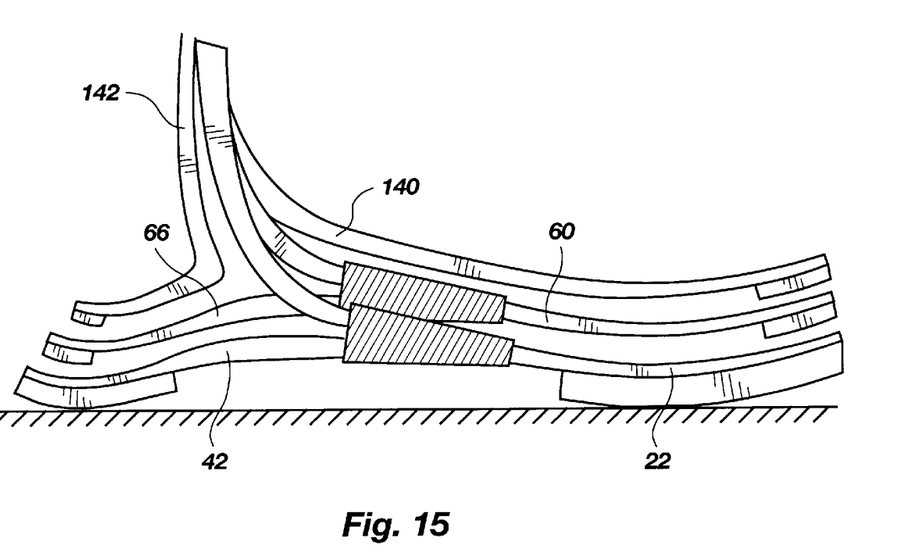
FIG. 15 is a side elevational view of an alternative embodiment of a prosthetic foot of the present invention.

As illustrated in FIG. 15, the prosthetic foot 10 may have multiple forefoot reinforcement members 60 and 140 and multiple heel reinforcement members 66 and 142. The reinforcement members may be disposed so that they engage at various intervals or stages of advancement throughout the full range of motion. The initial forefoot and heel reinforcement members 60 and 66 may act as primary reinforcement members and be engaged at a first stage of extreme range of motion, while the additional forefoot and heel reinforcement members 140 and 142 act as secondary reinforcement members and are engaged at a second stage of extreme range of motion.

It is to be understood that the described embodiments of the invention are illustrative only, and that modifications thereof may occur to those skilled in the art. Accordingly, this invention is not to be regarded as limited to the embodiments disclosed, but is to be limited only as defined by the appended claims herein.

What is claimed is:

1. A prosthetic foot comprising:
at least two resilient forefoot members disposed in lateral side-by-side relationship and having base ends coupled near an attachment location and extending forward to toe ends at a toe location, the at least two forefoot members having a range of motion with multiple stages of advancement including at least a normal range and an extreme range and having a resistance response to an applied force; and
at least one resilient forefoot reinforcement member having a base section coupled to at least one of the at least two forefoot members and extending to a free section proximal the toe location and spaced above the at least two resilient forefoot members, the free section being disposed within the extreme range of motion of the at least two forefoot members and freely movable with respect to the at least two forefoot members, the forefoot reinforcement member having a range of motion within the extreme range of motion of the at least two forefoot members, such that the forefoot reinforcement member influences the range of motion and resistance response of the at least two forefoot members.

2. The prosthetic foot of claim 1, wherein the at least one forefoot reinforcement member comprises
a first forefoot reinforcement member having a base section coupled to a first forefoot member and extending to a free section operable within the range of motion of the first forefoot member, and
a second forefoot reinforcement member having a base section coupled to a second forefoot member and extending to a free section operable within the range of motion of the second forefoot member.

3. The prosthetic foot of claim 1, wherein the at least one forefoot reinforcement member comprises
a primary forefoot reinforcement member having a base section coupled to at least one of the at least two forefoot members and extending to a free section operable within the range of motion of the at least two forefoot members, the primary forefoot reinforcement member having a range of motion within a primary extreme range of motion of the at least two forefoot members, and
a secondary forefoot reinforcement member having a base section coupled to at least one of the at least two forefoot members and extending to a free section operable within the range of motion of the at least two forefoot members, the secondary forefoot reinforcement member having a range of motion within a secondary extreme range of motion of the at least two forefoot members and within the range of motion of the primary forefoot reinforcement member.

4. The prosthetic foot of claim 1, further comprising
at least one resilient heel member having a base end coupled to at least one of the at least two resilient forefoot members and extending rearward to a heel end at a heel location, the at least one heel member having a range of motion including a normal range and an extreme range and having a resistance response to an applied force.

5. The prosthetic foot of claim 4, further comprising
at least one heel resilient reinforcement member having a base section coupled to at least one of the at least two forefoot members and extending to a free section operable within the range of motion of the at least one heel member, the free section being freely movable with respect to the at least one heel member, the heel reinforcement member having a range of motion within the extreme range of motion of the at least one heel member, such that the heel reinforcement member influences the range of motion and resistance response of the at least one heel member.

6. The prosthetic foot of claim 4, further comprising:

at least one heel reinforcement member having a base section coupled to at least one of the at least one forefoot reinforcement member and extending rearward to a free section operable within the range of motion of the at least one heel member.

7. The prosthetic foot of claim 4, wherein the at least one heel reinforcement member comprises a first heel reinforcement member having a base section coupled to a first heel member and extending to a free section operable within the range of motion of the first heel member, and a second heel reinforcement member having a base section coupled to a second heel member and extending to a free section operable within the range of motion of the second heel member.

8. The prosthetic foot of claim 4, wherein the at least one heel reinforcement member comprises a primary heel reinforcement member having a base section coupled to at least one of the at least two forefoot members and extending to a free section operable within the range of motion of the at least one heel member, the primary heel reinforcement member having a range of motion within a primary extreme range of motion of the at least one heel member, and a secondary heel reinforcement member having a base section coupled to at least one of the at least two forefoot members and extending to a free section operable within the range of motion of the at least one heel member, the secondary heel reinforcement member having a range of motion within a secondary extreme range of motion of the at least one heel member and within the range of motion of the primary heel reinforcement member.

9. The prosthetic foot of claim 1, further comprising a limiting means coupled between the free section of the at least one forefoot reinforcement member and the at least two forefoot members such that the limiting means prevents the at least two forefoot members from abruptly returning to an unstressed position when an applied force is removed.

10. The prosthetic foot of claim 9, wherein the limiting means comprises a strap.

11. The prosthetic foot of claim 1, further comprising a cushioning wear means disposed on the free section of the at least one forefoot reinforcement member for cushioning contact between the free section and the forefoot members or a surface.

12. The prosthetic foot of claim 1, further comprising a contact means disposed between the free section of the at least one forefoot reinforcement member and the at least two forefoot members such that the at least two forefoot members engage the at least one forefoot reinforcement member when the at least two forefoot members move from the normal range of movement to the extreme range of movement.

13. A prosthetic foot comprising:

at least two resilient forefoot members having base ends coupled near an attachment location and extending forward to toe ends at a toe location, the at least two forefoot members having a range of motion with multiple stages of advancement including at least a normal range and an extreme range and having a resistance response to an applied force;

at least one resilient heel member having a base end coupled to at least one of the at least two resilient forefoot members and extending rearward to a heel end at a heel location, the at least one heel member having a range of motion including a normal range and an extreme range and having a resistance response to an applied force; and at least one resilient reinforcement member having a base section coupled to at least one of the at least two forefoot members and extending to a free section proximal either the toe location or heel location and spaced above the at least two resilient forefoot members or heel members, the free section being disposed within the extreme range of motion of any of the at least two forefoot members or the at least one heel member and freely movable with respect to any of the at least two forefoot members or the at least one heel member, the reinforcement member having a range of motion within the extreme range of motion of any of the at least two forefoot members or the at least one heel member, such that the reinforcement member influences the range of motion and resistance response of any of the at least two forefoot members or the at least one heel member.

14. The prosthetic foot of claim 13, wherein the at least one reinforcement member has a base section coupled to at least one of the at least two forefoot members near the attachment section operable within the range of motion of the heel forefoot member.

15. The prosthetic foot of claim 13, wherein the at least one reinforcement member comprises a first forefoot reinforcement member having a base section coupled to a first forefoot member and extending to a free section operable within the range of motion of the first forefoot member, and a second forefoot reinforcement member having a base section coupled to a second forefoot member and extending to a free section operable within the range of motion of the second forefoot member.

16. The prosthetic foot of claim 13, wherein the at least one reinforcement member comprises a primary forefoot reinforcement member having a base section coupled to at least one of the at least two forefoot members and extending to a free section operable within the range of motion of the at least two forefoot members, the primary forefoot reinforcement member having a range of motion within a primary extreme range of motion of the at least two forefoot members, and a secondary forefoot reinforcement member having a base section coupled to at least one of the at least two forefoot members, and at least one heel reinforcement member having a base section coupled to at least one of the at least two forefoot members and extending rearward to a free section operable within the range of motion of the at least one heel member.

17. The prosthetic foot of claim 13, wherein the at least one reinforcement member has a base section coupled to at least one of the at least two forefoot members near the attachment location and extends rearward to a free section operable within the range of motion of the at least one heel member.

18. The prosthetic foot of claim 13, wherein the at least one reinforcement member has a base section coupled to at least one of the at least two forefoot members near an arch location and extends rearward to a free section operable within the range of motion of the at least one heel member.

19. The prosthetic foot of claim 13, wherein the at least one reinforcement member comprises
   a first heel reinforcement member having a base section coupled to a first heel member and extending to a free section operable within the range of motion of the first heel member, and
   a second heel reinforcement member having a base section coupled to a second heel member and extending to a free location and extends forward to a free section operable within the range of motion of at least one of the at least two forefoot members.

20. The prosthetic foot of claim 13, wherein the at least one reinforcement member comprises
   a primary heel reinforcement member having a base section coupled to at least one of the at least two forefoot members and extending to a free section operable within the range of motion of the at least one heel member, the primary heel reinforcement member having a range of motion within a primary extreme range of motion of the at least one heel member, and
   a secondary heel reinforcement member having a base section coupled to at least one of the at least two forefoot members and extending to a free section operable within the range of motion of the at least one heel member, the secondary heel reinforcement member having a range of motion within a secondary extreme range of motion of the at least one heel member and within the range of motion of the primary heel reinforcement member.

21. The prosthetic foot of claim 13, wherein the at least one reinforcement member comprises
   at least one forefoot reinforcement member having a base section coupled to at least one of the at least two forefoot members and extending forward to a free section operable within the range of motion of at least one of the at least two forefoot members and extending to a free section operable within the range of motion of the at least two forefoot members, the secondary forefoot reinforcement member having a range of motion within a secondary extreme range of motion of the at least two forefoot members and within the range of motion of the primary forefoot reinforcement member.

22. The prosthetic foot of claim 13, wherein the at least one reinforcement member comprises
   at least one forefoot reinforcement member having a base section coupled to at least one of the at least two forefoot members and extending forward to a free section operable within the range of motion of at least one of the at least two forefoot members, and
   at least one heel reinforcement member having a base section coupled to at least one of the at least one forefoot reinforcement member and extending rearward to a free section operable within the range of motion of the at least one heel member.

23. The prosthetic foot of claim 13, wherein the at least one reinforcement member comprises
   at least one heel reinforcement member having a base section coupled to at least one of the at least two forefoot members and extending rearward to a free section operable within the range of motion of the at least one heel member, and
   at least one forefoot reinforcement member having a base section coupled to at least one of the at least one heel reinforcement member and extending forward to a free section operable within the range of motion of at least one of the at least two forefoot members.

24. The prosthetic foot of claim 13, wherein the at least one reinforcement member has a base section coupled to at least one of the at least two forefoot members at an arch location and extends to a free end near the attachment location, the reinforcement member forming an arcuate section extending near the heel location.

25. The prosthetic foot of claim 13, wherein the at least one reinforcement member comprises
   a first reinforcement member having a base section coupled to at least one of the at least two forefoot members near an arch section and extending to a free section operable within the range of motion of the at least one heel member, the first reinforcement member forming an arcuate section, and
   a second reinforcement member having a base section coupled to at least one of the at least two forefoot members near the attachment section and extending to a free section near the arcuate section of the first reinforcement member.

26. The prosthetic foot of claim 13, further comprising
   a limiting means coupled between the free section of the at least one reinforcement member and any of the at least two forefoot members or at least one heel member such that the limiting means prevents any of the at least two forefoot members or at least one heel member from abruptly returning to an unstressed position when an applied force is removed.

27. The prosthetic foot of claim 26, wherein the limiting means comprises a strap.

28. The prosthetic foot of claim 13, further comprising
   a cushioning means disposed on the free section of the at least one reinforcement member for cushioning contact between the free section and the forefoot members, the heel member, or a surface.

29. The prosthetic foot of claim 13, further comprising
   a contact means disposed between the free section of the at least one reinforcement member and any of the at least two forefoot members or at least one heel member such that the at least two forefoot members or at least one heel member engage the at least one reinforcement member when the at least two forefoot members or at least one heel member move from the normal range of movement to the extreme range of movement.

30. A prosthetic foot comprising:
   at least two resilient forefoot members having base ends coupled near an attachment location and extending forward to toe ends at a toe location, the at least two forefoot members having a range of motion with multiple stages of advancement including at least a normal range and an extreme range and having a resistance response to an applied force;
   at least one resilient heel member having a base end coupled to at least one of the at least two resilient forefoot members and extending rearward to a heel end at a heel location, the at least one heel member having a range of motion including a normal range and an extreme range and having a resistance response to an applied force;
   at least one forefoot reinforcement member having a base section coupled to at least one of the at least two forefoot members and extending forward to a free section proximal the toe location and spaced above the at least two resilient forefoot members, the free section being disposed within the extreme range of motion of at least one of the at least two forefoot members, and at least one heel reinforcement member having a base section coupled to at least one of the at least one forefoot reinforcement member and extending rearward to a free section proximal the heel location and spaced above the at least one heel members, the free section being disposed within the extreme range of motion of the at least one heel member, such that the reinforcement members influence the range of motion and resistance response of the at least two forefoot members and the at least one heel member.

31. A method for simulating toe rotation and multiple uses of a natural foot, the method comprising the steps of:

(a) providing at least two resilient forefoot members having base ends coupled near an attachment location and extending forward to toe ends at a toe location, the at least two forefoot members having a range of motion with multiple stages of advancement including at least a normal range and an extreme range and having a resistance response to an applied force;

(b) providing at least one resilient forefoot reinforcement member having a base section coupled to at least one of the at least two forefoot members and extending to a free section proximal the toe location and spaced above the at least two resilient forefoot members, the free section being disposed within the extreme range of motion of the at least two forefoot members and freely moveable with respect to the at least two forefoot members, the forefoot reinforcement member having a range of motion within the extreme range of motion of the at least two forefoot members, such that the forefoot reinforcement member influences the range of motion and resistance response of the at least two forefoot members.

* * * * *